(12) United States Patent
Buchholz et al.

(10) Patent No.: US 7,009,062 B2
(45) Date of Patent: Mar. 7, 2006

(54) PROCESS FOR THE PREPARATION OF FLAVONE DERIVATIVES

(75) Inventors: Herwig Buchholz, Frankfurt (DE); Sophie Perruchon, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 34 days.

(21) Appl. No.: 10/470,773

(22) PCT Filed: Jan. 12, 2002

(86) PCT No.: PCT/EP02/00233

§ 371 (c)(1),
(2), (4) Date: Jul. 31, 2003

(87) PCT Pub. No.: WO02/060889

PCT Pub. Date: Aug. 8, 2002

(65) Prior Publication Data

US 2004/0059100 A1    Mar. 25, 2004

(30) Foreign Application Priority Data

Feb. 1, 2001    (DE) ............................... 101 04 350

(51) Int. Cl.
*C07D 311/30*    (2006.01)

(52) U.S. Cl. ..................................... 549/406

(58) Field of Classification Search ................. 549/406
See application file for complete search history.

(56) References Cited

U.S. PATENT DOCUMENTS 5,889,003 A    3/1999    Dhainaut et al.

FOREIGN PATENT DOCUMENTS

EP    0832886 A    4/1998

OTHER PUBLICATIONS

D. Nagarathnam: "A Short and Facile Synthetic Route to Hydroxylated Flavones." Journal of Organic Chemistry., Bd.56, 1991, Seiten 4887-7.

*Primary Examiner*—Taofiq Solola
(74) *Attorney, Agent, or Firm*—Millen, White, Zelano, Branigan, P.C.

(57) ABSTRACT

The invention relates to a process for the preparation of flavone derivatives in which a 2-hydroxyacetophenone compound is metallated using a lithium compound at low temperatures and subsequently reacted with a keto compound, and where the ratio of the molar equivalents of lithium compound to the 2-hydroxyacetophenone compound functional groups to be metallated is from 1 to 1.2. The resultant β-diketone compound is subsequently cyclized with warming in an acidic medium.

10 Claims, No Drawings

PROCESS FOR THE PREPARATION OF FLAVONE DERIVATIVES

This application is a 371 of PCT/EP02/00233, filed on Jan. 12, 2002.

The present invention relates to a process for the preparation of flavone derivatives in which a 2-hydroxyacetophenone compound is metallated using a lithium compound and subsequently reacted with a keto compound.

Polyphenol compounds, for example flavones which are hydroxylated on ring A, are the subject of intensive research and development work owing to their multifarious properties. These properties are, inter alia, the ability to block retroviral reverse transcriptases, including HIV transcriptase, likewise the property to block protein tyrosine kineases and serine/threonine kineases. In addition, compounds of this type have anticancer and chemo-preventive properties.

Some flavones which are hydroxylated on ring A likewise block syncytium formation caused by HIV. These flavones furthermore have antioxidative properties and are used as additives in foods and cosmetics.

Some processes are known for the preparation of flavones and derivatives thereof, all of which comprise a plurality of synthetic steps, some of which are complex, and are described, for example, in the publication by M. Cushman and D. Nagarathnam in: Tetrahedron Letters, 31, 6497–6500, 1990. These prove, in particular, to be disadvantageous in the synthesis of flavones which are hydroxylated on ring A since the phenolic hydroxyl groups of the intermediate compounds have to be protected as esters or ethers in order to prevent undesired substitution patterns. These protecting groups later have to be removed again in a further reaction step. Furthermore, partial removal of the protecting groups frequently occurs during the further successive synthetic steps, which firstly reduces the overall yield and makes isolation of the desired end product from a product mixture more difficult.

In order to avoid these disadvantages in the synthesis of flavones, M. Cushman and D. Nagarathnam have proposed in the above-mentioned publication and in "Journal of Organic Chemistry", 56, 4884–4887, 1991, deprotonating the phenolic hydroxyl groups using a large excess of lithium bis(trimethylsilyl)amide under homogeneous reaction conditions, and preparing the lithium enolate of the corresponding ketone. The carbon atom of the lithium enolate is subsequently acylated regioselectively using an aroyl chloride, directly giving a β-diketone intermediate, which is subsequently cyclised in an acidic medium. The large excess of the lithium base, which can only be removed with difficulty even in a plurality of purification steps, and the high price of the lithium base are disadvantageous in this process.

The object was therefore to develop a process for the preparation of flavone derivatives which avoids the above-mentioned disadvantages of the prior art and in particular enables simple and inexpensive access to flavone derivatives without complex purification steps.

This object is achieved in the process according to the invention in that the ratio of the molar equivalents of lithium compound to the 2-hydroxyacetophenone compound functional groups to be metallated is from 1 to 1.2.

Surprisingly, it has been found that the above-mentioned ratio allows complete metallation of all hydroxyl groups and the carbonyl group of the 2-hydroxyacetophenone compound. A ratio of less than 1 would result in incomplete metallation and thus in a large number of undesired by-products. By contrast, a ratio of greater than 1.2 means the use of a larger amount of the usually not inexpensive lithium compounds and the entrainment of lithium compounds in all further subsequent steps, in particular purification steps.

The lithium compound is preferably selected from inorganic lithium compounds since they are available inexpensively and readily in large amounts. They furthermore offer the advantage that they are sparingly soluble or even insoluble in organic solvents, meaning that they can easily be filtered out of the reaction mixture after a metallation reaction carried out under heterogeneous conditions if they are employed in excess.

In a preferred embodiment of the process according to the invention, the ratio of lithium compound to the 2-hydroxyacetophenone compound functional groups to be metallated is precisely 1. The result of this is that no lithium compounds which may still be dissolved occur as impurities in the end product since they usually cannot be removed from the intermediates and end products even by purification steps, such as recrystallisation.

The metallation is advantageously carried out in an ethereal solvent since this supports the metallation reaction through its polarity due to the formation of Li solvates, increasing the basicity of the lithium base.

The 2-hydroxyacetophenone employed in the process according to the invention preferably has the following structure:

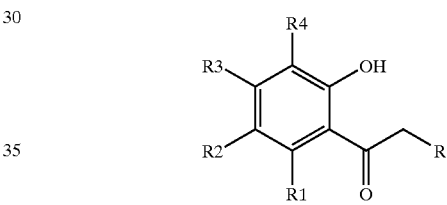

where $R_1$ to $R_4$ are hydrogen or a functional group selected from hydroxyl, alkyl, alkenyl, ether, ester, aryl, O-glycosyl, alkoxy, alkenoxy, aryloxy, halogen, nitro and amino, and may be identical or different and/or for $R_n$–$R_{n+1}$ for n=1, 2 or 3, may be part of a ring system, and where R is hydrogen or an alkoxy group.

If an isoflavone derivative is to be prepared, R may also be a phenyl or substituted phenyl group, such as, for example, 4-methoxyphenyl.

The keto compound for carrying out the process according to the invention has the following structure:

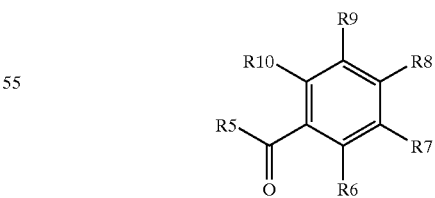

where $R_6$ to $R_{10}$ are hydrogen or a functional group selected from hydroxyl, alkyl, alkenyl, ether, ester, aryl, O-glycosyl, alkoxy, alkenoxy, aryloxy, halogen, nitro and amino, and may be identical or different and/or where $R_n$–$R_{n+1}$ where n=6, 7, 8 or 9, may be part of a ring system, and where $R_5$ can be a halide, alkoxy or ester group.

The great variability of the starting materials employed thus allows virtually all known flavones, flavonols and flavonoids originating therefrom to be prepared simply and inexpensively in a one-pot reaction by means of the process according to the invention.

The hydroxyl groups of the 2-hydroxyacetophenone compound are preferably unprotected. Complex reactions for the introduction and removal of protecting groups are thus avoided, so that the reaction proceeds particularly simply.

Further advantages and embodiments of the invention arise from the description and the working examples.

It goes without saying that the features mentioned above and still to be explained below can be used not only in the respective combination indicated, but also in other combinations or alone without leaving the scope of the present invention.

In general terms, the process according to the invention is a one-pot synthesis of flavone derivatives in accordance with the following reaction:

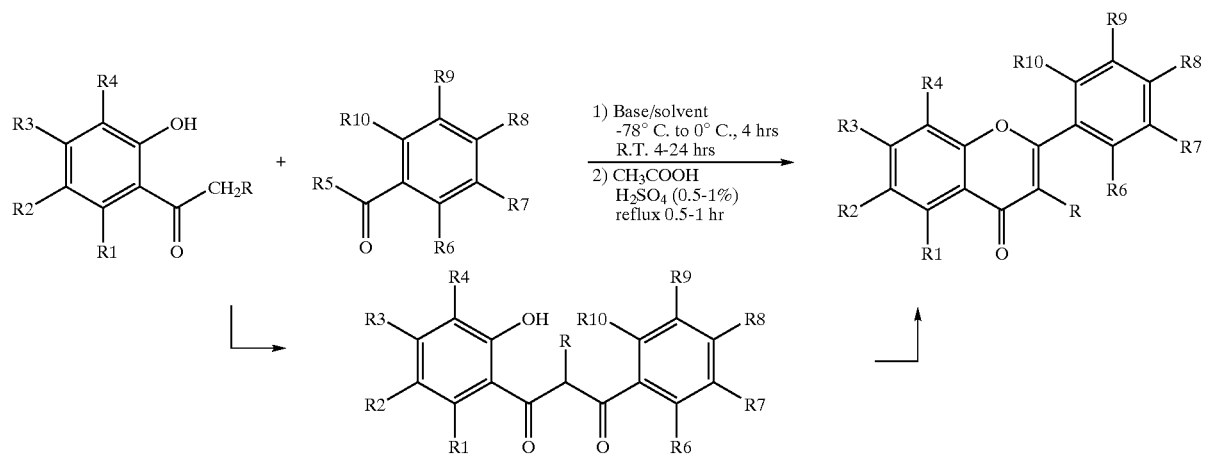

For the purposes of the present invention, the term flavone derivatives is firstly taken to mean compounds which have the flavone basic structure (2-phenyl-4H-1-benzopyran-4-one) in common. In the present case, these also furthermore include flavonols having the basic structure of 2-phenyl-3-hydroxy-4H-1-benzopyran-4-one and flavonoids, i.e., for example, glycosides of flavones or flavonols which are dyes widely found in plants and in which a carbohydrate radical, such as, for example, glucose, is bonded to the hydroxyl group in position 3 of the flavonol. Flavones and flavone derivatives usually have one or more hydroxyl groups both on ring A and on the phenyl ring in the 2-position. Furthermore, isoflavones (3-phenyl-4H-1-benzopyran-4-one), chromones and aurones also fall under the definition used in accordance with the invention.

Besides the flavone derivatives mentioned in the following working examples, examples of flavone derivatives prepared by means of the process according to the invention furthermore include, as an incomplete and non-restrictive list, apigenin, acacetin, chrysin, flavone, 7,4-dihydroxyflavone, 7,3',4'-tirhydroxyflavone, 6-hydroxy-4'-methoxyflavone, luteolin, diosmetin, tricetin, hypolaetin, prosogerin, 3,7-dihydroxyflavone, luteolin 3',4',5'-trimethyl ether, 7,3', 4',5'-tetrahydroxyflavone, tricetin 3',4',5'-trimethyl ether, resokaempferol, kaempferol, isokaemferide, kaempferide, ermanin, fisetin, herbacetin, 3,7,8,4'-tetrahydroxyflavone, quercetin, dillenetin, transilitin, gossypetin, myricetin, annulatin and hibiscetin.

Flavones, in particular flavonoids and flavonoid mixtures, are used, for example, in the food and cosmetic industries, where they are increasing in importance. Monoglycosidated flavonoids, such as, for example, isoquercetin, in particular, are distinguished by good absorbability in the human body.

where R, in the case of the 2-hydroxyacetophenone compound, can be hydrogen or an alkoxy group. If R is hydrogen, a flavone in the narrower sense is formed; in the case of an alkoxy group, a flavonol is formed.

In the case of the keto compounds, $R_5$ is chloride, i.e. the compound is an acid chloride, an alkoxy group, i.e. the compound is an ester, or an ester group, i.e. the compound is an acid anhydride. The use of different groups also allows, depending on the substrate employed, variation and precise selection of the reaction time. For example, the reaction time on use of an acid chloride or acid anhydride is between 2 and 6 hours, usually between 4 and 5 hours. On use of an ester or on use of silylated protecting groups, the reaction time is more than 8 hours, usually more than 10 hours, but often also about 16–20 hours.

Firstly, the 2-hydroxyacetophenone compound is condensed with the ketone and a lithium compound in dry THF at low temperatures (from −78° C. to −50° C.), giving a stable diketone intermediate. At temperatures above −50° C., the reaction either does not proceed at all or proceeds too quickly, i.e. with undesired by-products or alternatively with decomposition of the starting material, and consequently the range from −78° C. to −50° C. is preferred. The diketone is subsequently cyclised under acidic conditions at 95–100° C. in order to give a flavone derivative.

$R_1$, $R_2$, $R_3$, $R_4$, $R_5$, $R_6$, $R_7$, $R_8$, $R_9$ and $R_{10}$ here can be hydrogen, a functional group selected from hydroxyl, alkyl, alkenyl, ether, ester, aryl, O-glycosyl, alkoxy, alkenoxy, aryloxy, halogen, nitro and amino, and may be identical or different and/or, where $R_n$–$R_{n+1}$, where n=1, 2, 3 and/or 6, 7, 8 or 9, may be part of a ring system.

Particularly suitable lithium bases used in a process according to the invention are the lithium bases listed below:

LiNH$_2$, LiN(CH$_3$)$_2$, LiN(C$_2$H$_5$)$_2$, LiNCH(CH$_3$)$_2$ (LDA), Me$_3$CLi, PhCH$_2$Li, Ph$_2$CHLi, Ph$_3$CLi, LiCN, LiC(NO$_3$)$_3$, LiC(CN)$_3$, LiN(C$_6$H$_{11}$)$_2$, LiN(CH$_2$)$_2$, LiCH$_3$, LiC$_2$H$_5$, LiCH(CH$_3$)$_2$, LiC$_4$H$_9$, LiCH$_2$CH(CH$_3$)$_2$, LiC$_6$H$_{13}$, LiPh, LiCH$_3$COCHCOCH$_3$, LiClO, LiClO$_4$, LiIO$_4$, Li$_2$O, LiOH, LiOCH$_3$, LiOC$_2$H$_5$, LiOC$_4$H$_9$, LiOPh, LiOCOPh, lithium enolates of the general formula LiOCR=CR'$_{12}$, where R and R' are an aliphatic or aromatic radical, LiOSi(CH$_3$)$_3$, Li(Si(CH$_3$)$_3$)$_2$, Li$_2$CO$_3$, lithium-2,2,6,6-tetramethylpiperidine (LiTMP).

Of these, as described above, particular preference is given to the purely inorganic lithium compounds or the lithium compounds whose usually organic radical is bonded to the lithium atom via inorganic atoms (O, N or Si).

The solvent for carrying out the metallation reaction is preferably, as described above, an ethereal solvent, for example diethyl ether, tetrahydrofuran (THF) or dibutyl ether. However, it is likewise possible to use other polar solvents, such as methyl ethyl ketone and the like, but also, depending on the hydroxyacetophenone employed, apolar solvents, such as, for example, n-hexane, heptane, benzene, toluene, etc.

For further illustration of the invention, reference is made to the following working examples:

The sources of supply of the substances used are as follows:

| Name | Manufacturer | Article No. | Purity |
|---|---|---|---|
| Lithium hydroxide | Merck KGaA | 105691 | LAB 98% |
| THF | Merck KGaA | 108107 | Seccolov dried |
| Methanol | Merck KGaA | 106009 | Pro analysi |
| Chloroform | Merck KGaA | 102445 | Pro analysi |
| Hydrochloric acid, fuming | Merck KGaA | 100314 | Extra pure 37% |
| Sulfuric acid | Merck KGaA | 100731 | Pro analysi 95–97% |
| Glacial acetic acid | Merck KGaA | 100063 | Pro analysi 100% |
| 4-Methoxybenzoyl chloride | Merck KGaA | 820106 | for synthesis >98% |
| 3,4-Dimethoxybenzoyl chloride | Aldrich | 25, 804-0 | 98% |
| Isophthaloyl chloride | Merck KGaA | 804808 | for synthesis >99% |
| 9-Fluorenone-4-carbonyl chloride | Aldrich | 24, 958-0 | 97% |
| 2,4-Dihydroxyacetophenone | Merck KGaA | 822027 | for synthesis >98% |
| 2,5-Dihydroxyacetophenone | Merck KGaA | 818284 | for synthesis >98% |
| 2,6-Dihydroxyacetophenone | Merck KGaA | 820472 | for synthesis >99% |
| 2,4,6-Trihydroxyacetophenone | Aldrich | T-6, 480-2 | hydrate, 98% |
| Piperonylbenzoyl chloride | Aldrich | 37, 889-5 | 99% |
| 4-Chlorobenzoyl chloride | Merck KGaA | 802618 | >98% |
| 4-Nitrobenzoyl chloride | Merck KGaA | 806772 | >98% |

EXAMPLE 1

Dry, pulverulent lithium hydroxide (29.1 mmol, 5 equivalents) is added in one portion to a well-stirred solution of 2,4,6-trihydroxyacetophenone (5.828 mmol) in dry THF (5 ml) under an argon atmosphere at −78° C. The reaction mixture is stirred at −78° C. for one hour and subsequently at about 0° C. for two hours. After the mixture has been re-cooled to −78° C., a solution of 3,4-dimethoxybenzoyl chloride (5.9 mmol) in THF (10 ml) is added in one portion. The mixture is stirred at −78° C. for one hour and at room temperature for 4 hours until the starting material has disappeared. The reaction mixture is emptied into a mixture of ice (150 g) and concentrated HCl (10 ml) and extracted with chloroform (3×50 ml). The solvents are removed from the dried extracts, and the residue is dried under reduced pressure for 24 hours. Glacial acetic acid (30 ml) and sulfuric acid (0.2 ml) are added to the residue, and the mixture is heated at 95–100° C. for from 30 minutes to one hour under an argon atmosphere. Approximately one third of the acetic acid is stripped off, and the residue is emptied into water. The precipitated product is filtered, washed and dried and recrystallised in methanol, giving 3',4'-dimethoxy-5-hydroxy-7-(3,4-dimethoxybenzoyl)oxyflavone (luteolin derivative); $^1$H NMR (250 MHz, CDCl$_3$): δ=3.9 (s, 12H), 6.65–6.70 (m, 2 H), 6.95–7.00 (m, 3 H), 7.35 and 7.67 (AB dd, 1 H), 7.53 and 7.85 (AB dd, 2 H), 12.85 (s, 1 H); $^{13}$C NMR DEPT (250 MHz, DMSO-d$^6$): δ=56.16 (s), 77.23 (s), 101.23 (s), 104.96 (s), 105.61 (s), 108.83 (s), 110.51 (s), 111.26 (s), 112.44 (s), 120.35 (s), 124.77 (s); EI-MS (70 eV) m/e (rel. abund.)=478; UV (2-propanol): λ=271 nm, 344 nm.

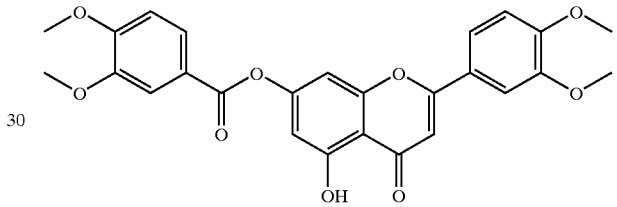

EXAMPLE 2

Dry, pulverulent lithium hydroxide (18 mmol, 3.6 equivalents) is added in one portion to a well-stirred solution of 2,4-dihydroxyacetophenone (5 mmol) in dry THF (5 ml) under an argon atmosphere at −78° C. The reaction mixture is stirred at −78° C. for one hour and subsequently at about 0° C. for two hours. After the mixture has been re-cooled to −78° C., a solution of 3,4-dimethoxybenzoyl chloride (5.9 mmol) in THF (10 ml) is added in one portion. The mixture is stirred at −78° C. for one hour and at room temperature for 4 hours until the starting material has disappeared. The reaction mixture is emptied into a mixture of ice (150 g) and concentrated HCl (5 ml) and extracted with chloroform (3×50 ml). The solvents are removed from the dried extracts, and the residue is dried under reduced pressure for 24 hours. Glacial acetic acid (30 ml) and sulfuric acid (0.2 ml) are added to the residue, and the mixture is heated at 95–100° C. for from 30 minutes to one hour under an argon atmosphere. Approximately one third of the acetic acid is stripped off, and the residue is emptied into water. The precipitated product is filtered, washed and dried and recrystallised in methanol, giving 3',4'-dimethoxy-7-hydroxyflavone. $^1$H NMR (250 MHz, DMSO-d$^6$): δ=3.85 (d, 6 H), 6.85–8.00 (m, 7 H), 10.72 (s, 1 H); $^{13}$C NMR (250 MHz, DMSO-d$^6$): δ=56.08 (s), 56.22 (s), 102.95 (s), 105.82 (s), 109.76 (s), 112.11 (s), 115.19 (s), 116.51 (s), 119.38 (s), 123.97 (s), 126.80 (s), 149.40 (s), 152.10 (s), 157.79 (s), 162.41 (s), 162.94 (s), 176.70 (s); EI-MS (70 eV) m/e (rel. abund.)=298; UV (2-propanol): λ=236 nm, 332 nm.

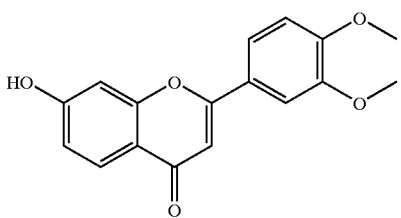

EXAMPLE 3

Dry, pulverulent lithium hydroxide (19.7 mmol, 3 equivalents) is added in one portion to a well-stirred solution of 2,6-dihydroxyacetophenone (6.6 mmol) in dry THF (5 ml) under an argon atmosphere at −78° C. The reaction mixture is stirred at −78° C. for one hour and subsequently at −10° C. for two hours. After the mixture has been re-cooled to −78° C., a solution of 3,4-dimethoxybenzoyl chloride (6 mmol) in THF (10 ml) is added in one portion. The mixture is stirred at −78° C. for one hour and at room temperature for 4 hours until the starting material has disappeared. The reaction mixture is emptied into a mixture of ice (150 g) and concentrated HCl (5 ml) and extracted with chloroform (3×50 ml). The solvents are removed from the dried extracts, and the residue is dried under reduced pressure for 24 hours. Glacial acetic acid (30 ml) and sulfuric acid (0.2 ml) are added to the residue, and the mixture is heated at 95–100° C. for from 30 minutes to one hour under an argon atmosphere. Approximately one third of the acetic acid is stripped off, and the residue is emptied into water. The precipitated product is filtered, washed and dried and recrystallised in methanol, giving 3',4'-dimethoxy-5-hydroxyflavone. $^1$H NMR (250 MHz, CDCl$_3$): δ=4.00 (d, 6 H), 6.60–7.60 (md, 7 H), 12.65 (s, 1 H); $^{13}$C NMR CDP (250 MHz, CDCl$_3$): δ=54.71 (s), 103.48 (s), 105.57 (s), 107.45 (s), 109.76 (s), 118.93 (s), 122.24 (s), 133.80 (s), 147.93 (s), 151.06 (s), 159.39 (s), 163.17 (s), 182.04 (s); EI-MS (70 eV) m/e (rel. abund.)=298; UV (2-propanol): λ=248 nm, 342.5 nm.

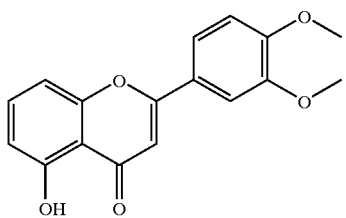

EXAMPLE 4

Dry, pulverulent lithium hydroxide (19.5 mmol, 3 equivalents) is added in one portion to a well-stirred solution of 2,6-dihydroxyacetophenone (6.6 mmol) in dry THF (5 ml) under an argon atmosphere at −78° C. The reaction mixture is stirred at −78° C. for one hour and subsequently at −10° C. for two hours. After the mixture has been re-cooled to −78° C., a solution of isophthaloyl chloride (3.3 mmol) in THF (10 ml) is added in one portion. The mixture is stirred at −78° C. for one hour and at room temperature for 4 hours until the starting material has disappeared. The reaction mixture is emptied into a mixture of ice (150 g) and concentrated HCl (5 ml) and extracted with chloroform (3×50 ml). The solvents are removed from the dried extracts, and the residue is dried under reduced pressure for 24 hours. Glacial acetic acid (30 ml) and sulfuric acid (0.2 ml) are added to the residue, and the mixture is heated at 95–100° C. for from 30 minutes to one hour under an argon atmosphere. Approximately one third of the acetic acid is stripped off, and the residue is emptied into water. The precipitated product is filtered, washed and dried and recrystallised in methanol, giving 3'-(5-hydroxychromonyl)-5-hydroxyflavone. EI-MS (70 eV) m/e (rel. abund.)=398.

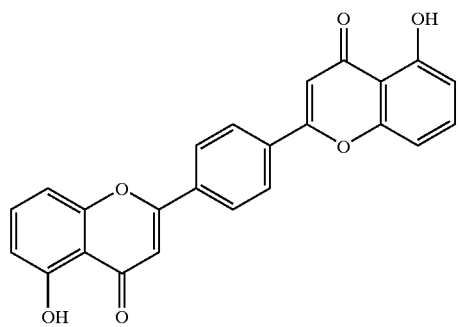

EXAMPLE 5

Dry, pulverulent lithium hydroxide (19.7 mmol, 3 equivalents) is added in one portion to a well-stirred solution of 2',5'-dihydroxyacetophenone (6.4 mmol) in dry THF (5 ml) under an argon atmosphere at −78° C. The reaction mixture is stirred at −78° C. for one hour and subsequently at −10° C. for two hours. After the mixture has been re-cooled to −78° C., a solution of 4-methoxybenzoyl chloride (6.5 mmol) in THF (10 ml) is added in one portion. The mixture is stirred at −78° C. for one hour and at room temperature for 4 hours until the starting material has disappeared. The reaction mixture is emptied into a mixture of ice (150 g) and concentrated HCl (5 ml) and extracted with chloroform (3×50 ml). The solvents are removed from the dried extracts, and the residue is dried under reduced pressure for 24 hours. Glacial acetic acid (30 ml) and sulfuric acid (0.2 ml) are added to the residue, and the mixture is heated at 95–100° C. for from 30 minutes to one hour under an argon atmosphere. Approximately one third of the acetic acid is stripped off, and the residue is emptied into water. The precipitated product is filtered, washed and dried and recrystallised in methanol, giving 4'-methoxy-6-hydroxyflavone. $^1$H NMR (250 MHz, d$^6$-DMSO): δ=3.73 (s, 3H), 6.6–8.5 (m, 8 H), 12.5 (s, 10 H); NMR (250 MHz, d$^6$-DMSO): δ=56 (s), 94.9 (s), 114.0 (s), 117.6 (s), 118.9 (s), 122.2 (s), 126.6 (s), 127.2 (s), 150.5 (s), 152.0 (s), 161.2 (s), 168.8 (s), 187.0 (s) EI-MS (70 eV) m/e (rel. abund.)=268; UV (2-propanol): λ=254 nm, 323 nm.

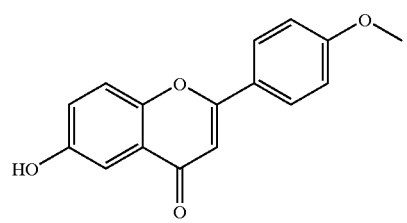

EXAMPLE 6

Dry, pulverulent lithium hydroxide (11.55 mmol, 3.3 equivalents) is added in one portion to a well-stirred solution of 2,4-dihydroxyacetophenone (3.22 mmol) in dry THF (5 ml) under an argon atmosphere at −78° C. The reaction mixture is stirred at −78° C. for one hour and subsequently at −10° C. for two hours. After the mixture has been re-cooled to −78° C., a solution of 9-fluorenone-4-carbonyl chloride (3.3 mmol) in THF (10 ml) is added in one portion. The mixture is stirred at −78° C. for one hour and at room temperature for 4 hours until the starting material has disappeared. The reaction mixture is emptied into a mixture of ice (150 g) and concentrated HCl (5 ml) and extracted with chloroform (3×50 ml). The solvents are removed from the dried extracts, and the residue is dried under reduced pressure for 24 hours. Glacial acetic acid (30 ml) and sulfuric acid (0.2 ml) are added to the residue, and the mixture is heated at 95–100° C. for from 30 minutes to one hour under an argon atmosphere. Approximately one third of the acetic acid is stripped off, and the residue is emptied into water. The precipitated product is filtered, washed and dried and recrystallised in methanol, giving 2-(9-fluorenon-4-yl) hydroxychromone. EI-MS (70 eV) m/e (rel. abund.)=340.

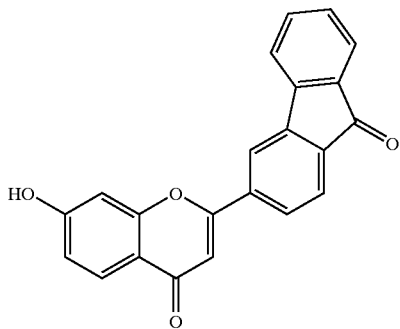

EXAMPLE 7

Dry, pulverulent lithium hydroxide (40 mmol, 2 equivalents) is added in one portion to a well-stirred solution of 2'-hydroxy-4',5'-dimethyleneoxyacetophenone (20 mmol) in dry THF (100 ml) under an argon atmosphere at −78° C. The reaction mixture is stirred at −78° C. for one hour and subsequently at −10° C. for two hours. After the mixture has been re-cooled to −78° C., a solution of piperonylbenzoyl chloride (22 mmol) in THF (100 ml) is added in one portion. The mixture is stirred at −78° C. for one hour and at room temperature for 4 hours until the starting material has disappeared. The reaction mixture is emptied into a mixture of ice (400 g) and concentrated HCl (15 ml) and extracted with dichloromethane (4×60 ml). The solvents are removed from the dried extracts, and the residue is dried under reduced pressure for 24 hours. Glacial acetic acid (220 ml) and sulfuric acid (1.1 ml) are added to the residue, and the mixture is heated at 95–100° C. for from 30 minutes to one hour under an argon atmosphere. Approximately one third of the acetic acid is stripped off, and the residue is emptied into water. The precipitated product is filtered, washed and dried and recrystallised in methanol, giving 3',4',6,7-bis(dimethyleneoxy)flavone. EI-MS (70 eV) m/e (rel. abund.)=310.

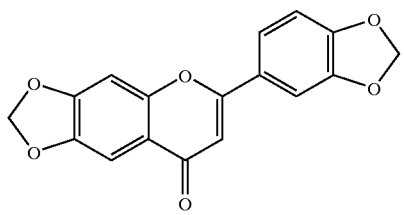

EXAMPLE 8

Dry, pulverulent lithium hydroxide (51 mmol, 4 equivalents) is added in one portion to a well-stirred solution of 2',6'-dihydroxyacetophenone (12.8 mmol) in dry THF (40 ml) under an argon atmosphere at −78° C. The reaction mixture is stirred at −78° C. for one hour and subsequently at −10° C. for two hours. After the mixture has been re-cooled to −78° C., a solution of 4-chlorobenzoyl chloride (13.97 mmol) in THF (20 ml) is added in one portion. The mixture is stirred at −78° C. for one hour and at room temperature for 4 hours until the starting material has disappeared. The reaction mixture is emptied into a mixture of ice (400 g) and concentrated HCl (16 ml) and extracted with dichloromethane (3×50 ml). The solvents are removed from the dried extracts, and the residue is dried under reduced pressure for 24 hours. Glacial acetic acid (100 ml) and sulfuric acid (0.5 ml) are added to the residue, and the mixture is heated at 95–100° C. for from 30 minutes to one hour under an argon atmosphere. Approximately one third of the acetic acid is stripped off, and the residue is emptied into water. The precipitated product is filtered, washed and dried and recrystallised in methanol, giving 4'-chloro-5-hydroxy-flavone. $^1$H NMR (250 MHz, CDCl$_3$): δ=6.7–8.0 (m, 7H), 12.5 (s, 10 H); EI-MS (70 eV) m/e (rel. abund.)=272; UV (2-propanol): λ=213 nm, 301 nm, 275 nm, 338 nm.

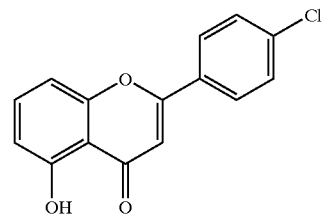

EXAMPLE 9

Dry, pulverulent lithium hydroxide (52.5 mmol, 4 equivalents) is added in one portion to a well-stirred solution of 2',6'-dihydroxyacetophenone (13.1 mmol) in dry THF (40 ml) under an argon atmosphere at −78° C. The reaction mixture is stirred at −78° C. for one hour and subsequently at −10° C. for two hours. After the mixture has been re-cooled to −78° C., a solution of 4-nitrobenzoyl chloride (14.46 mmol) in THF (40 ml) is added in one portion. The mixture is stirred at −78° C. for one hour and at room temperature for 4 hours until the starting material has disappeared. The reaction mixture is emptied into a mixture of ice (400 g) and concentrated HCl (16 ml) and extracted with dichloromethane (3×50 ml). The solvents are removed from the dried extracts, and the residue is dried under reduced pressure for 24 hours. Glacial acetic acid (100 ml) and sulfuric acid (0.5 ml) are added to the residue, and the mixture is heated at 95–100° C. for from 30 minutes to one hour under an argon atmosphere. Approximately one third of the acetic acid is stripped off, and the residue is emptied into water. The precipitated product is filtered, washed and dried and recrystallised in methanol, giving 4'-nitro-5-hydroxy-flavone. $^1$H NMR (250 MHz, CDCl$_3$): δ=6.75–8.5 (m, 7H), 12.3 (s, 1OH); EI-MS (70 eV) m/e (rel. abund.)=283.

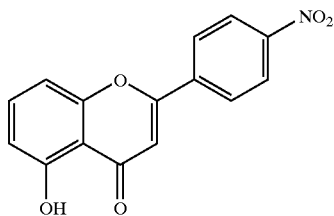

The invention claimed is:

1. A process for preparing a compound of the formula:

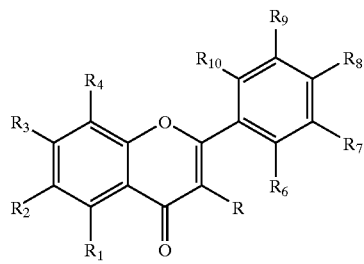

comprising metallating a compound of the formula:

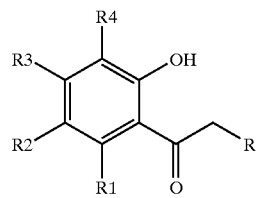

wherein $R_1$–$R_4$, are, independently, hydrogen or a group of hydroxyl, alkyl, alkenyl, ether, ester, aryl, O-glycosyl, alkoxy, alkenoxy, aryloxy, halogen, nitro or amino, and/or any two adjacent $R_1$–$R_4$ may combine to form a ring system, and R is hydrogen, an alkoxy group or an optionally substituted phenyl group, with an inorganic lithium compound, and subsequently reacting the metallated compound with a keto compound of the formula:

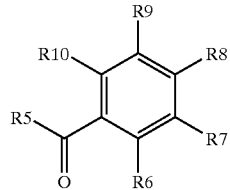

wherein $R_6$–$R_{10}$ are, independently, hydrogen or a group of hydroxyl, alkyl, alkenyl, ether, ester, aryl, O-glycosyl, alkoxy, alkenoxy, aryloxy, halogen, nitro or amino, and/or any two adjacent $R_6$–$R_{10}$ may combine to form a ring system, and $R_5$ is a halide, alkoxy or ester group, wherein the ratio of molar equivalents of the lithium compound to the functional groups to be metallated on the 2-hydroxyacetophenone compound is 1–1.2.

2. A process according to claim 1, wherein the ratio of the molar equivalents of lithium compound to the 2-hydroxyacetophenone compound functional groups to be metallated is about 1.

3. A process according to claim 1, wherein the metallation is conducted in an ethereal solvent.

4. A process according to claim 1, wherein the hydroxyl groups of the 2-hydroxyacetophenone compound are unprotected.

5. A process according to claim 1, wherein the inorganic lithium compound is LiNH$_2$, LiCN, LiC(NO$_3$)$_3$, LiC(CN)$_3$, LiClO$_4$, Li$_2$O, LiOH or Li$_2$CO$_3$.

6. A process according to claim 1, wherein the inorganic lithium compound is LiOH.

7. A process according to claim 1, wherein the keto compound is isophthaloyl chloride or 9-fluorenone-4-carbonyl chloride.

8. A process according to claim 1, wherein the 2-hydroxyacetophenone compound is 2,4-dihydroxyacetophenone, 2,5-dihydroxyacetophenone, 2,6-dihydroxyacetophenone, or 2,4,6-trihydroxyacetophenone.

9. A process according to claim 1, wherein the keto compound is 4-methoxybenzoyl chloride, 3,4-dimethoxybenzoyl chloride, isophthaloyl chloride, 9-fluorene-4-carbonyl chloride, piperonylbenzoyl chloride, 4-chlorobenzoyl chloride, or 4-nitrobenzoyl chloride.

10. A process for preparing a compound of the formula:

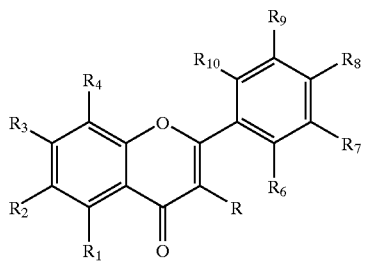

comprising metallating a compound of the formula:

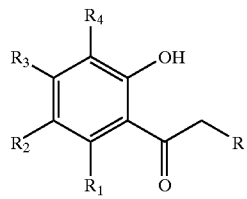

wherein $R_1$–$R_4$, are, independently, hydrogen or a group of hydroxyl, alkyl, alkenyl, ether, ester, aryl, O-glycosyl, alkoxy, alkenoxy, aryloxy, halogen, nitro or amino, and/or any two adjacent $R_1$–$R_4$ may combine to form a ring system, and R is hydrogen, an alkoxy group or an optionally substituted phenyl group, with an inorganic lithium compound, and subsequently reacting the metallated compound with a compound of the formula:

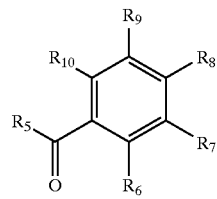

wherein $R_6$–$R_{10}$ are, independently, hydrogen or a group of hydroxyl, alkyl, alkenyl, ether, ester, aryl, O-glycosyl, alkoxy, alkenoxy, aryloxy, halogen, nitro or amino, and/or any two adjacent $R_6$–$R_{10}$ may combine to form a ring system, and $R_5$ is a halide, alkoxy or ester group.

* * * * *